US012661235B2

(12) United States Patent
Arcos et al.

(10) Patent No.: US 12,661,235 B2
(45) Date of Patent: Jun. 23, 2026

(54) INTERVERTEBRAL DEVICES

(71) Applicant: AXIS SPINE TECHNOLOGIES LTD, St. Albans (GB)

(72) Inventors: Jonathan Arcos, St. Albans (GB);
Christopher Reah, St. Albans (GB);
Nicholas Sandham, London (GB);
David Powell, London (GB)

(73) Assignee: ASIX SPINE TECHNOLOGIES LTD, Reading (GB)

( * ) Notice: Subject to any disclaimer, the term of this patent is extended or adjusted under 35 U.S.C. 154(b) by 170 days.

(21) Appl. No.: 18/766,011

(22) Filed: Jul. 8, 2024

(65) Prior Publication Data

US 2025/0073044 A1 Mar. 6, 2025

Related U.S. Application Data

(63) Continuation of application No. 17/763,193, filed as application No. PCT/GB2020/052317 on Sep. 24, 2020, now Pat. No. 12,029,657.

(30) Foreign Application Priority Data

Sep. 24, 2019 (GB) ...................................... 1913777

(51) Int. Cl.
*A61F 2/44* (2006.01)
*A61F 2/30* (2006.01)
(52) U.S. Cl.
CPC ... *A61F 2/4455* (2013.01); *A61F 2002/30112* (2013.01); *A61F 2002/30266* (2013.01); *A61F 2002/30331* (2013.01); *A61F 2002/3054* (2013.01); *A61F 2002/30556* (2013.01); *A61F 2002/30736* (2013.01)

(58) Field of Classification Search
CPC .......... A61F 2/44; A61F 2/4455; A61F 2/447; A61F 2/4425; A61F 2/30
See application file for complete search history.

*Primary Examiner* — Christopher J Beccia
(74) *Attorney, Agent, or Firm* — LIU & LIU

(57) ABSTRACT

An intervertebral fusion device is disclosed. The intervertebral fusion device comprises a superior component 40, an inferior component 60 and a core component 10. The superior component 40 has a superior component top side and a superior component bottom side and is configured to be received in an intervertebral space between first and second vertebrae whereby the superior component top side abuts against the first vertebra. The inferior component 60 has an inferior component top side and an inferior component bottom side and is configured to be received in the intervertebral space whereby the inferior component bottom side abuts against the second vertebra. The superior component bottom side and the inferior component top side oppose each other when the superior and inferior components 40, 60 are received in the intervertebral space. The core component 10 is configured for insertion between the superior and inferior components 40, 60 whereby a separation between the superior and inferior components is determined. The core component 10 comprises a retention mechanism which moves between a contracted condition and an expanded condition. The core component 10 is insertable between the superior and inferior components 40, 60 when the retention mechanism is in the contracted condition. The retention mechanism inter-engages with the superior component 40 and the inferior component 60 when in the expanded condition and when the core component 10 is received between the superior and inferior components to thereby present resistance to movement of the core component from between the superior and inferior components.

18 Claims, 6 Drawing Sheets

INTERVERTEBRAL DEVICES

This application is a continuation of U.S. patent application Ser. No. 17/763,193 filed on Mar. 23, 2022, which is a 371 of International Application No. PCT/GB2020/052317 filed on Sep. 24, 2020, which claims priority of GB Patent Application No. 1913777.7 filed on Sep. 24, 2019. These applications are fully incorporated by reference as if fully set forth herein.

FIELD OF THE INVENTION

The present invention relates to intervertebral devices and more specifically to intervertebral fusion devices.

BACKGROUND TO THE INVENTION

Adjacent vertebrae in the spinal column are coupled to each other by an intervertebral disc. The intervertebral disc holds the adjacent vertebrae together and functions as a cushion between the vertebrae whilst allowing for relative movement of the vertebrae. Problems with intervertebral discs arise from one or more of a range of diseases and conditions. A surgical procedure, such as spinal fusion, may be used to address such problems. A typical spinal fusion procedure involves partial or full removal of a problematic intervertebral disc and installation of an intervertebral device in the place of the partially or fully removed intervertebral disc.

Known intervertebral devices are of varied form and function. Many known intervertebral devices are configured to provide for adjustment of height and functional spine unit angle to address differing extents of removal of an intervertebral disc, differing anatomy and spinal deformity. Furthermore, ease of assembly, installation, including reduced impaction loads during insertion, and disassembly are design objects for known intervertebral devices aside from issues of manufacturability and cost. Some known intervertebral devices are characterised by their complexity with such complexity being liable to result in compromise on ease of assembly, installation and disassembly, in compromise on long-term reliability, or in risk to the patient, such as from wear of material from the intervertebral device over time and loss of spinal correction.

The present inventors have become appreciative of shortcomings of known intervertebral devices, such as the shortcomings mentioned above. The present invention has been devised in light of the inventors' appreciation of such shortcomings. It is therefore an object for the present invention to provide an improved intervertebral device and more specifically an improved intervertebral fusion device. It is a further object for the present invention to provide an improved method of installing an intervertebral device in an intervertebral space between first and second adjacent vertebrae and more specifically an improved method of installing an intervertebral fusion device.

STATEMENT OF INVENTION

According to a first aspect of the present invention there is provided an intervertebral fusion device comprising:

a superior component having a superior component top side and a superior component bottom side, the superior component being configured to be received in an intervertebral space between first and second vertebrae whereby the superior component top side abuts against the first vertebra;

an inferior component having an inferior component top side and an inferior component bottom side, the inferior component being configured to be received in the intervertebral space between the first and second vertebrae whereby the inferior component bottom side abuts against the second vertebra, the superior component bottom side and the inferior component top side opposing each other when the superior and inferior components are received in the intervertebral space; and a core component configured for insertion between the superior and inferior components whereby a separation between the superior and inferior components is determined, wherein the core component comprises a retention mechanism which moves between a contracted condition and an expanded condition, the core component being insertable between the superior and inferior components when the retention mechanism is in the contracted condition, and the retention mechanism inter-engaging with the superior component and the inferior component when in the expanded condition to thereby present resistance to movement of the core component from between the superior and inferior components.

The intervertebral fusion device comprises three main components, i.e. a superior component, an inferior component and a core component. In use, the superior and inferior components are placed in an intervertebral space between first and second vertebrae formed by at least partial removal of a problematic intervertebral disc. The superior component has a superior component top side and a superior component bottom side. The superior component is configured, such as in respect of shape and/or size, to be received in an intervertebral space between first and second vertebrae whereby the superior component top side abuts against the first vertebra or what might remain of a partially removed intervertebral disc. The inferior component has an inferior component top side and an inferior component bottom side. The inferior component is configured, such as in respect of shape and/or size, to be received in the intervertebral space between the first and second vertebrae whereby the inferior component bottom side abuts against the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully received between the superior and inferior components as described below.

The core component is configured, such as in respect of shape and/or size, for insertion between the superior and inferior components. In use, the core component may be inserted between the superior and inferior components when the superior and inferior components have been placed in the intervertebral space, as described above. When inserted such that it is substantially fully received between the superior and inferior components, the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc. Differing heights of intervertebral fusion device may be provided by selection from plural core components of different height. The intervertebral fusion device may be an implant.

As mentioned above, an intervertebral disc functions as a shock absorber. An intervertebral disc is therefore under load with the pattern of loading varying and repeating over an extended period. When installed in place of the intervertebral disc, the intervertebral fusion device is likewise under load with such loading being liable to eject the core component from between the superior and inferior components. Usually, such loading provides for ejection to an inconsiderable extent at any one time. Nevertheless, such fractional ejection can become appreciable over time. Ejection is a risk for a core component of any shape, such as a core component having substantially parallel upper and lower surfaces, and not just a risk for the wedge-shaped core component described below. The core component therefore comprises a retention mechanism which is operative to present resistance, and more specifically a barrier, to ejection of the core component from between the superior and inferior components.

The retention mechanism moves between a contracted condition and an expanded condition. The core component is insertable between the superior and inferior components when the retention mechanism is in the contracted condition. The retention mechanism inter-engages with the superior component and the inferior component when in the expanded condition and when the core component is received, and more specifically substantially fully received, between the superior and inferior components to thereby present resistance to movement, and more specifically ejection, of the core component from between the superior and inferior components. The retention mechanism may interlock with the superior component and the inferior component when in the expanded condition to present a barrier to ejection of the core component from between the superior and inferior components.

According to an embodiment, movement of the retention mechanism between the contracted and expanded conditions may be in the medial-lateral direction (otherwise, transverse direction direction). The medial-lateral direction may be orthogonal to a direction of insertion of the core component between the superior and inferior components (otherwise, anterior-posterior direction) and orthogonal to a direction of separation of the superior and inferior components (otherwise, the spine axis). Where the core component has an upper side and a lower side, the medial-lateral direction may be orthogonal to a direction of separation of the upper and lower sides and orthogonal to a direction of separation of posterior and anterior sides of the core component.

The core component may be of greater extent in the transverse direction when in the expanded condition than when in the contracted condition by virtue of movement of the retention mechanism. When in the expanded condition, the retention mechanism may cooperate with a surface profile defined on each of the superior and inferior components whereby the core component inter-engages with the superior component and the inferior component to present resistance to movement of the core component from between the superior and inferior components. When in the contracted condition, the core component may be of smaller extent in the transverse direction whereby the retention mechanism may be moved past the surface profiles to allow the core component to be inserted between the superior and inferior components.

The core component may be integrally formed and the retention mechanism may be integral to the core component. The core component may therefore be structured to be operative as the retention mechanism. The core component may be configured such that it is compressible in the transverse direction, such as by hand, whereby the core component moves from the expanded condition to the contracted condition. The core component may be inserted between the superior and inferior components when compressed and therefore in the contracted condition. When the core component is properly inserted between the superior and inferior components, the core component may move from the contracted condition to the expanded condition. When the core component is in the expanded condition, the core component may inter-engage with the superior and inferior components to present resistance to movement of the core component from between the superior and inferior components.

The core component may be resiliently compressible whereby the core component returns from the contracted condition to the expanded condition when the core component is received between the superior and inferior components to bring the core component into inter-engagement with the superior and inferior components. The core component may return from the contracted condition to the expanded condition upon release of force which keeps the core component in the contracted condition.

The core component may be structured for resilient compression. The core component may have a posterior side and an anterior side, the posterior and anterior sides being oppositely directed and the posterior side being received between the superior and inferior components before the anterior side when the core component is inserted between the superior and inferior components. The core component may further have first and second lateral sides which each face in a direction orthogonal to a direction of insertion of the core component and to a direction of separation of the inferior and superior components, with the first and second lateral sides facing in opposite directions. The core component may be structured such that the first and second lateral sides at the anterior side may not be compressed towards each other when a compressive force is applied. The core component may be further structured such that the first and second lateral sides at the posterior side may be compressed towards each other when the compressive force is applied.

The core component may have a substantially rigid structure between the first and second lateral sides at the anterior side and may have a resiliently yielding structure between the first and second lateral sides at the posterior side.

The core component may comprise a rigid anterior component, a first lateral component and a second lateral component. The rigid anterior component may define the anterior side and may extend between the first and second lateral components, which respectively define the first and second lateral sides.

The rigid anterior component, the first lateral component and the second lateral component may be integrally formed.

The core component may further comprise a posterior structure, which defines the posterior side, and which extends between the first and second lateral components, the posterior structure providing for movement at the posterior structure of the first and second lateral components together and apart to thereby provide for compression and expansion.

The posterior structure may comprise a first posterior component and a second posterior component, the first posterior component being attached to, and more specifically integrally formed with, the first lateral component, and the second posterior component being attached to, and more specifically integrally formed with, the second lateral component. Furthermore, the distal end of the first posterior component and the distal end of the second posterior component may face each other and may be spaced apart from each other when in the expanded or uncompressed condition.

The retention mechanism may comprise a retention member which is inserted between the distal end of the first posterior component and the distal end of the second posterior component when in the expanded or uncompressed condition. The retention member may maintain separation between the distal end of the first posterior component and the distal end of the second posterior component. The retention member may, for example, have the form of a wedge or a screw.

When the first and second lateral components are compressed towards each other at the posterior side, the distal ends of the first and second posterior components move towards each other to allow for compression and for the contracted condition to be achieved. Maximum compression may be achieved when the distal ends of the first and second posterior components abut.

In view of the core component being substantially incompressible between the first and second lateral sides at the anterior side, each of the first and second lateral components may bend whereby the distal ends of the first and second posterior components move towards each other. The first and second lateral components may have a structure, such as in respect of dimensions, and/or may be formed of appropriate material whereby the first and second lateral components bend upon application of a compressive force to the first and second lateral components at the posterior side. Furthermore, the first and second lateral components may have an inherently sprung structure, by virtue of at least one of dimensions, shape and material, whereby they return to their unbent condition upon release of the compressive force.

Each of the first and second lateral components may be solid whereby the lateral component is free from cavities. Each of the first and second posterior components may be solid whereby the posterior component is free from cavities. The anterior component may have a box frame structure.

When the core component is in the uncompressed or expanded condition, a distance between the first and second lateral sides at the posterior side may be greater than a distance between the first and second lateral sides at the anterior side. The core component may therefore taper from the posterior side towards the anterior side. As described further below, the taper may provide for inter-engagement with the superior and inferior components to present resistance to movement of the core component from between the superior and inferior components.

When the core component is in the compressed or contracted condition, a distance between the first and second lateral sides at the posterior side may be no greater than a distance between the first and second lateral sides at the anterior side. The core component may therefore be capable of insertion between the superior and inferior components.

As mentioned above, the retention mechanism may cooperate with a surface profile defined on each of the superior and inferior components whereby the core component inter-engages with the superior component and the inferior component to present resistance to movement of the core component from between the superior and inferior components. Further to this, the core component may define surface profiles which cooperate with surface profiles of the superior and inferior components to present resistance to movement of the core component from between the superior and inferior components.

The surface profiles of the core component and of the superior and inferior components may also inter-engage to restrict movement of the superior and inferior components away from the core component as the core component is slidably received between the superior and inferior components.

The surface profiles of the core component will now be described in more detail. The core component may comprise a first pair of upper and lower lateral protrusions projecting from the first lateral side and a second pair of upper and lower lateral protrusions projecting from the second lateral side. The upper and lower lateral protrusions in each pair may be spaced apart from each other in a direction of separation of the upper and lower sides of the core component.

Each of the upper and lower lateral protrusions may extend along a respective lateral side in a direction between the anterior and posterior sides. Where the core component is not wedge shaped, the upper and lower lateral protrusions may be parallel. Where the core component is wedge shaped, as described below, the upper and lower lateral protrusions may be at an angle to each other and more specifically at an angle corresponding to angulation of superior and inferior components determined by the wedge-shaped core component.

Each of the superior and inferior components may define first and second keyways, the first keyway being towards a first lateral side of the component and the second keyway being towards a second lateral side of the component, the first and second keyways opposing each other. Furthermore, each of the first and second keyways may extend from an anterior side of the component towards the posterior side of the component. Each keyway may be shaped to slidably receive a respective one of the lateral protrusions projecting from the core component. Thus, the first keyway on the superior component may receive the upper lateral protrusion on the first lateral side of the core component, the second keyway on the superior component may receive the upper lateral protrusion on the second lateral side of the core component, the first keyway on the inferior component may receive the lower lateral protrusion on the first lateral side of the core component, and the second keyway on the inferior component may receive the lower lateral protrusion on the second lateral side of the core component. Slidable reception of lateral protrusions in keyways may hold the superior component, core component and inferior component together as the core component is slidably inserted between the superior and inferior components.

Each lateral protrusion may extend from adjacent the anterior side of the core component part way towards the posterior side. Each lateral protrusion may extend no more than halfway and more specifically no more than quarter of the way towards the posterior side. Reception of the lateral protrusions in their respective keyways may therefore hold the superior and inferior components to the core component at the anterior side of the core component.

Each keyway may extend from adjacent an anterior side of the respective one of the superior and inferior components part way towards the posterior side.

Each keyway may extend from the anterior side by a distance corresponding to the distance extended by the lateral protrusion.

Each lateral protrusion may define an inclined surface which extends from a distal end of the protrusion towards the core component. Each keyway may define an inclined surface which extends from a distal end of the part of the superior or inferior component defining the keyway in a transverse direction away from the distal end. The inclined surfaces of the lateral protrusion and the keyway may be of corresponding angle whereby the two inclined surfaces may abut and allow for sliding movement of the core component relative to the superior or inferior component. Furthermore, the inclined surfaces of the lateral protrusion and the keyway may allow for the core component to be narrower between distal ends of the parts of the superior or inferior component defining the keyways on opposite sides of the superior or inferior component than the width of the superior or inferior component between the bases of the keyways on opposite sides of the superior or inferior component. This may allow for the core component and the superior or inferior component to be held together despite the core component being narrower.

The first and second keyways on each of the superior and inferior components may taper in a direction from the posterior side to the anterior side. A distance between the first and second keyways may therefore be less at the anterior side than towards the posterior side. As described above, the core component may be tapered in the same direction when in the expanded condition. The lateral protrusions on the core component may therefore bear against the first and second keyways to present resistance to movement of the core component relative to the respective one of the superior and inferior components in a direction opposite to the direction of insertion of the core component between the superior and inferior components.

An angle of taper, i.e. in a direction from the posterior side to the anterior side, of between 1 and 10 degrees to an anterior to posterior axis of the core component has been found to provide appropriate performance in respect of providing sufficient retention of the core component between the superior and inferior components whilst, for example, exerting no undue bending strain on the first and second lateral components. An angle of taper of between 2 and 3 degrees may be preferred.

The core component may comprise upper and lower posterior protrusions which project from the posterior side of the core component. The upper and lower posterior protrusions may be spaced apart from each other in a direction between the upper and lower sides of the core component.

Each of the upper and lower posterior protrusions may extend part way along the posterior side and perhaps about halfway along the posterior side. Furthermore, each of the upper and lower posterior protrusions may be substantially centrally located on the posterior side.

Where the posterior structure comprises first and second posterior components, as described above, a first upper posterior protrusion and a first lower posterior protrusion may project from the first posterior component and a second upper posterior protrusion and a second lower posterior protrusion may project from the second posterior component.

Each of the superior and inferior components may define a posterior formation which is shaped to receive a respective one of the upper and lower posterior protrusions. The posterior formation may be a recess.

Each posterior protrusion and its corresponding posterior formation may be shaped to draw the core component and the respective one of the superior and inferior components progressively closer together during a last stage of insertion of the core component between the superior and inferior components. The posterior protrusion and its corresponding posterior formation may start to inter-engage when the core component is at least 80% inserted. Each posterior protrusion and its corresponding posterior formation may define an inclined surface, the two inclined surfaces sliding over each other to draw the core component and the respective one of the superior and inferior components progressively closer together.

In a different form of the embodiment, the retention mechanism may not be integral to the core component. This different form of the embodiment will now be described.

The non-integral retention mechanism may be mounted on the core component. As described above, the retention mechanism moves between a contracted condition, in which the core component is insertable between the superior and inferior components, and an expanded condition, in which the retention mechanism inter-engages with the superior and inferior components. Furthermore, and as described above, movement of the retention mechanism between the contracted and expanded conditions may be in a transverse direction.

The retention mechanism may comprise first and second retention mechanism portions. The core component may have first and second lateral sides which each face in a direction orthogonal to a direction of insertion of the core component and to a direction of separation of the inferior and superior components, with the first and second lateral sides facing in opposite directions. In the contracted condition the first retention mechanism portion may not protrude beyond a periphery of the core component on the first lateral side and the second retention mechanism portion may not protrude beyond a periphery of the core component on the second lateral side. In the expanded condition the first retention mechanism portion may protrude beyond the periphery of the core component on the first lateral side and the second retention mechanism portion may protrude beyond the periphery of the core component on the second lateral side.

When the first and second retention mechanism portions protrude beyond their respective peripheries, the first retention mechanism portion may be received in a first retention mechanism recess, and more specifically notch, in the superior component and a first retention mechanism recess, and more specifically notch, in the inferior component, and the second retention mechanism portion may be received in a second retention mechanism recess, and more specifically notch, in the superior component and a second retention mechanism recess, and more specifically notch, in the inferior component. Resistance to movement of the core component from between the superior and inferior components may thus be presented. As described further below, the retention mechanism may be structured such that the first and second retention mechanism portions move together between the contracted and expanded conditions in dependence on user operation.

The first and second retention mechanism recesses of the superior component may be located respectively towards first and second lateral sides of the superior component. Furthermore, the first and second retention mechanism recesses of the superior component may face each other. The first and second retention mechanism recesses of the inferior component may be located respectively towards first and second lateral sides of the inferior component. Furthermore, the first and second retention mechanism recesses of the inferior component may face each other.

According to a first approach, the retention mechanism may have a spring bias which biases the first and second retention mechanism portions towards the expanded condition. According to a second approach, the retention mechanism may have a spring bias which biases the first and second retention mechanism portions towards the contracted condition.

In both of the first and second approaches, the retention mechanism comprises a sprung member with the first and second retention mechanism portions being comprised in the sprung member. More specifically, a first end of the sprung member may constitute the first retention mechanism portion and a second, opposite end of the sprung member may constitute the second retention mechanism portion. The sprung member may be bendable upon application of a bending force to change between the contracted and expanded conditions.

In the first approach, the sprung member may be structured such that it is longer and therefore in the expanded condition when no energy is stored in the sprung member. The sprung member may, for example, be straight when in the expanded condition. Upon application of bending force, the sprung member may be bent such that its length decreases to put the sprung member in the contracted condition. The sprung member according to the first approach may be brought into use by applying bending force before the core component is inserted between the superior and inferior components. When the core component is received between the superior and inferior components, the bending force may be released. Upon the core component being properly received between the superior and inferior components, the energy stored in the sprung member causes the length of the sprung member to increase whereby the first and second retention mechanism portions may inter-engage with the superior and inferior components.

In the second approach, the sprung member may be structured such that it is shorter and therefore in the contracted condition when no energy is stored in the sprung member. Upon application of bending force, the sprung member may be bent such that its length increases to put the sprung member in the expanded condition. The sprung member according to the second approach may be brought into use by inserting the core component between the superior and inferior component. When the core component is properly received between the superior and inferior components, bending force may be applied to the sprung member to increase its length and thereby put it in the expanded condition.

Furthermore, the sprung member may be structured such that another bending force, which is oppositely directed to the bending force used to put the sprung member into the expanded condition, is applied to move the sprung member from the expanded condition back towards the contracted condition. The sprung member may thus remain in the expanded condition and without continued application of force or holding of the sprung member in the expanded condition.

According to an alternative embodiment, movement of the retention mechanism between the contracted and expanded conditions may be in a direction extending between upper and lower sides of the core component. The direction of movement may therefore be orthogonal to the transverse direction of movement according to the previously described embodiment and orthogonal to a direction extending between posterior and anterior sides of the core component.

In the alternative embodiment the retention mechanism may comprise first and second retention mechanism portions. In the contracted condition the first retention mechanism portion may not protrude beyond a periphery of the core component at its upper side and the second retention mechanism portion may not protrude beyond a periphery of the core component at its lower side. In the expanded condition the first retention mechanism portion may protrude beyond the periphery of the core component at the upper side and the second retention mechanism portion may protrude beyond the periphery of the core component at the lower side.

When the first and second retention mechanism portions protrude beyond their respective peripheries, the first retention mechanism portion may be received in a first retention mechanism recess in the superior component, and the second retention mechanism portion may be received in a second retention mechanism recess in the inferior component. The first retention mechanism recess may be defined in the superior component bottom side and the second retention mechanism recess may be defined in the inferior component top side.

Resistance to movement of the core component from between the superior and inferior components may thus be presented. As described further below, the retention mechanism may be structured such that the first and second retention mechanism portions move together between the contracted and expanded conditions in dependence on user operation.

The retention mechanism may be located towards a posterior side of the core component. When the retention mechanism is in the expanded condition, the first and second retention mechanism portions may therefore protrude from the core component towards the posterior side of the core component.

The retention mechanism may further comprise a driving device which cooperates with the first and second retention mechanism portions to push the first and second retention mechanism portions apart to thereby put the retention mechanism in the expanded condition.

The driving device and each of the first and second retention mechanism portions may have cooperating surface profiles which push the first and second retention mechanism portions apart as the driving device is moved relative to the first and second retention mechanism portions. The driving device may be moved relative to the first and second retention mechanism portions in a direction extending between posterior and anterior sides of the core component.

The driving device may define a first frustroconical surface. The first retention mechanism portion may define a first part of a second frustroconical surface and the second retention mechanism portion may define a second part of the second frustroconical surface. The first and second retention mechanism portions may be located such that the first and second parts of the second frustroconical surface oppose each other. The first and second parts of the second frustroconical surface may therefore together define the second frustroconical surface, albeit with a gap between the first and second retention mechanism portions. When the driving device is moved relative to the first and second retention mechanism portions, the first frustroconical surface pushes against each of the first and second parts of the second frustroconical surface and thereby forces the first and second retention mechanism portions apart.

The driving device may comprise a first threaded portion which is threadedly received in a second threaded portion comprised in the core component. Rotation of the driving device may therefore cause the first threaded portion to move linearly in relation to the second threaded portion whereby the driving device moves linearly in relation to the first and second retention mechanism portions. The second threaded portion may be located closer to the posterior side of the core component than the first and second retention mechanism portions.

Each of the first and second retention mechanism portions may be mounted for rotation on the core component. Furthermore, each of the first and second retention mechanism portions may be structured such that a distal end of the retention mechanism portion moves between not protruding beyond the periphery of the core component and protruding beyond the periphery of the core component as the retention mechanism portion rotates on the core component. The first and second retention mechanism portions may, for example, be rotated on the core component by the driving device described above.

The upper side and a lower side of the core component may be inclined to each other. The core component may therefore have the form of a wedge. Furthermore, the upper side and a lower side may not meet at an acute angle whereby the core component has the form of a frustum of a wedge. The core component and the inferior and superior components may be configured for insertion of the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having upper and lower sides of different inclinations. Such selection may be combined with selection from a plurality of core components having different heights.

The superior component, the inferior component and the core component may be separate components. Having separate inferior and superior components and core component means that the components may be introduced to the intervertebral space more gently compared with known single piece intervertebral fusion devices which often need to be hammered into place. Such a less gentle insertion process may damage the intervertebral fusion device, may increase time required for the intervertebral fusion device to settle in the intervertebral space, and may result in trauma to vertebral bodies, adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and degree of spinal alignment and/or correction. Each of the superior component, the inferior component and the core component may be integrally formed. The superior component and the inferior component may not engage with each other, other than by way of the core component.

Each of the inferior and superior components may have the form of a plate, albeit a plate having structures thereon that provide for mechanical engagement with the core component, whereby it is thin relative to its length and width. At least one of the superior component top side and the inferior component bottom side may be shaped in the coronal or sagittal planes, for example domed, to enhance fit and contact with the adjacent vertebrae.

The core component, the superior component and the inferior component may be formed by the like of casting, moulding or printing. Alternatively, the core component, the superior component and the inferior component may be formed by the like of machining or stamping.

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK, carbon reinforced PEEK or UHMWPE (Ultra High Molecular Weight PolyEthylene). In forms of the invention, the core component may be formed by 3D printing whereby the core component has the form of a 3D lattice. The aforementioned materials may be used to form the core component by way of 3D printing.

Where the intervertebral fusion device is in accordance with the different form of the first described embodiment above, the sprung member may be formed of a metal such as MP35N, titanium or nitinol.

When assembled, the intervertebral fusion device may have a range of length by width from 20 mm by 15 mm to 65 mm by 50 mm. Where there is an oblique intervertebral fusion device, the range of length by width may be from 20 mm by 15 mm to 40 mm by 35 mm. Where there is an anterior intervertebral fusion device, the range of length by width may be from 20 mm by 20 mm to 50 mm by 50 mm. Where there is a lateral intervertebral fusion device, the range of length by width may be from 40 mm by 18 mm to 65 mm by 40 mm. A height of the intervertebral fusion device may be 5 mm to 15 mm at the posterior aspect.

References herein to anterior or to anterior aspect are to the anterior aspect of the intervertebral fusion device itself and not to the anterior aspect of the patient. The anterior aspect of the intervertebral fusion device itself therefore means the aspect at which the core component is inserted between the superior and inferior components. Correspondingly, references herein to posterior or to posterior aspect are to the posterior aspect of the intervertebral fusion device itself and not to the posterior aspect of the patient. The anterior and posterior aspects are oppositely directed. The intervertebral fusion device may be an anterior, anterior oblique, lateral or direct lateral intervertebral fusion device.

According to a second aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

positioning the superior component and the inferior component relative to each other such that the superior component bottom side and the inferior component top side oppose each other;

inserting the core component between the superior and inferior components whereby a separation between the superior and inferior components is determined; and disposing the intervertebral fusion device in the intervertebral space such that the superior component top side abuts against the first vertebra and the inferior component bottom side abuts against the second vertebra, wherein the core component comprises a retention mechanism which moves between a contracted condition and an expanded condition, the core component being insertable between the superior and inferior components when the retention mechanism is in the contracted condition, and the retention mechanism inter-engaging with the superior component and the inferior component when in the expanded condition to thereby present resistance to movement of the core component from between the superior and inferior components.

The intervertebral fusion device may be installed in an intervertebral space by positioning the superior component and the inferior component relative to each other in the intervertebral space before the core component is inserted between the superior and inferior components. Alternatively, the intervertebral fusion device may be installed in an intervertebral space by positioning the superior component and the inferior component relative to each other at a location apart from the intervertebral space and inserting the core component between the superior and inferior components at this location before the thus assembled intervertebral fusion device is installed in the intervertebral space.

Further embodiments of the second aspect of the present invention may comprise one or more features of the first aspect of the present invention.

BRIEF DESCRIPTION OF DRAWINGS

The present invention will now be described by way of example only with reference to the following drawings, of which:

FIG. 4 shows a third embodiment of intervertebral fusion device;

FIG. 5A shows a fourth embodiment of intervertebral fusion device; and

FIG. 5B shows the core component of the fourth embodiment from a different angle from FIG. 5A.

DESCRIPTION OF EMBODIMENTS

Figures 1A, 1B, 1C, 1D:
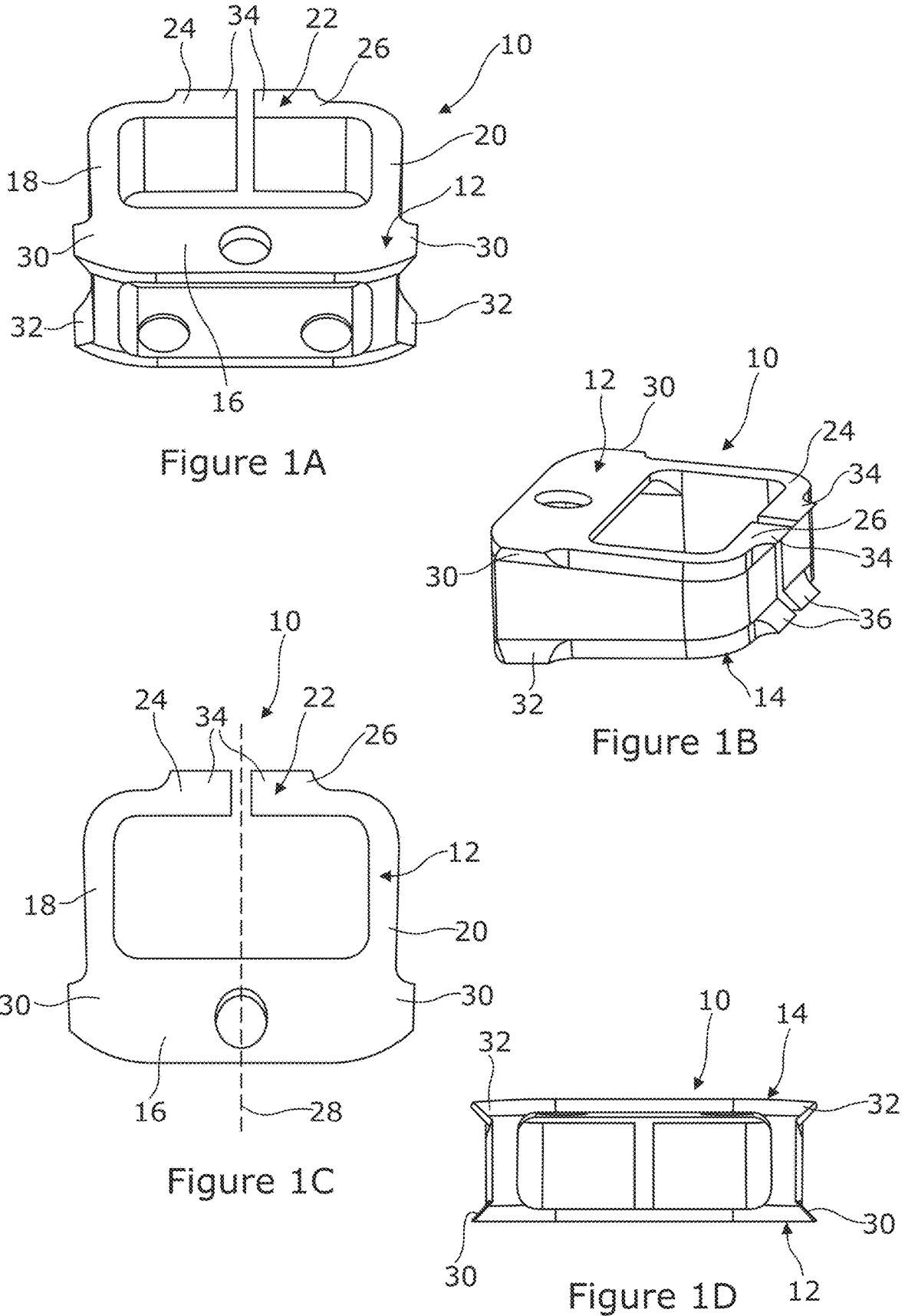
FIG. 1A is a perspective view from above and the anterior side of a core component according to a first embodiment of the present invention.
FIG. 1B is a perspective view from above, a lateral side and the posterior side of the core component of the first embodiment.
FIG. 1C is a plan view of the core component of the first embodiment.
FIG. 1D is a view from the anterior side of the core component of the first embodiment.
Figure 1E:
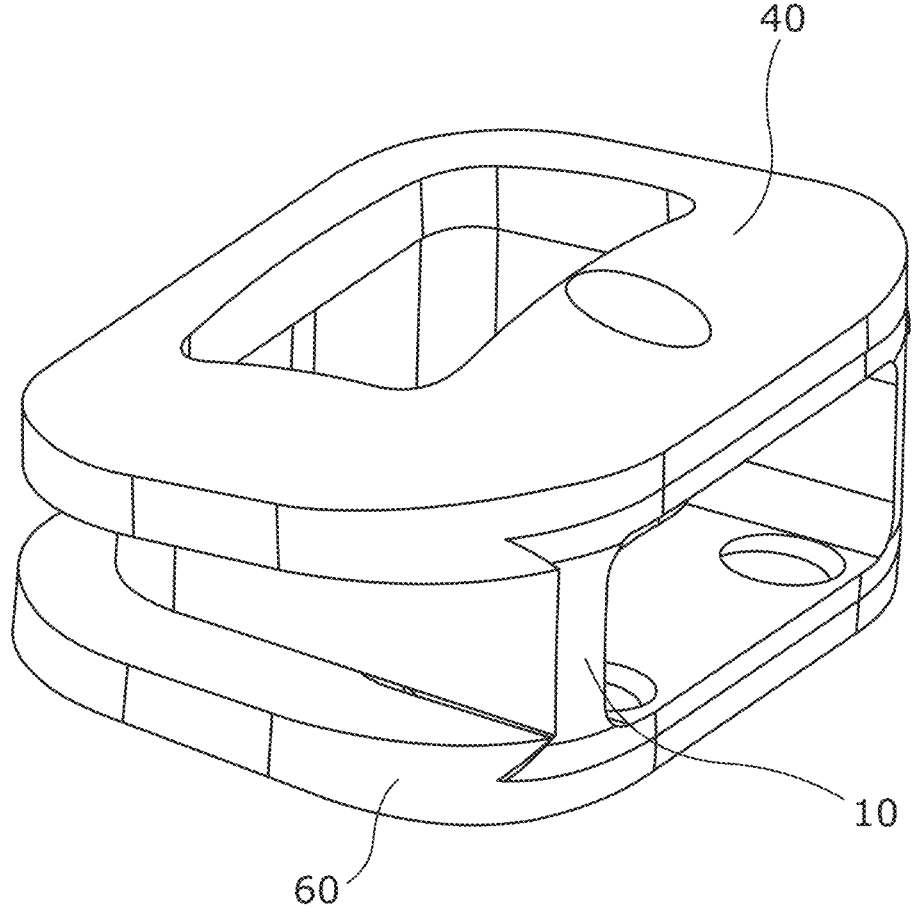
FIG. 1E is a perspective view of the first embodiment of intervertebral fusion device when assembled.
Figure 2A:
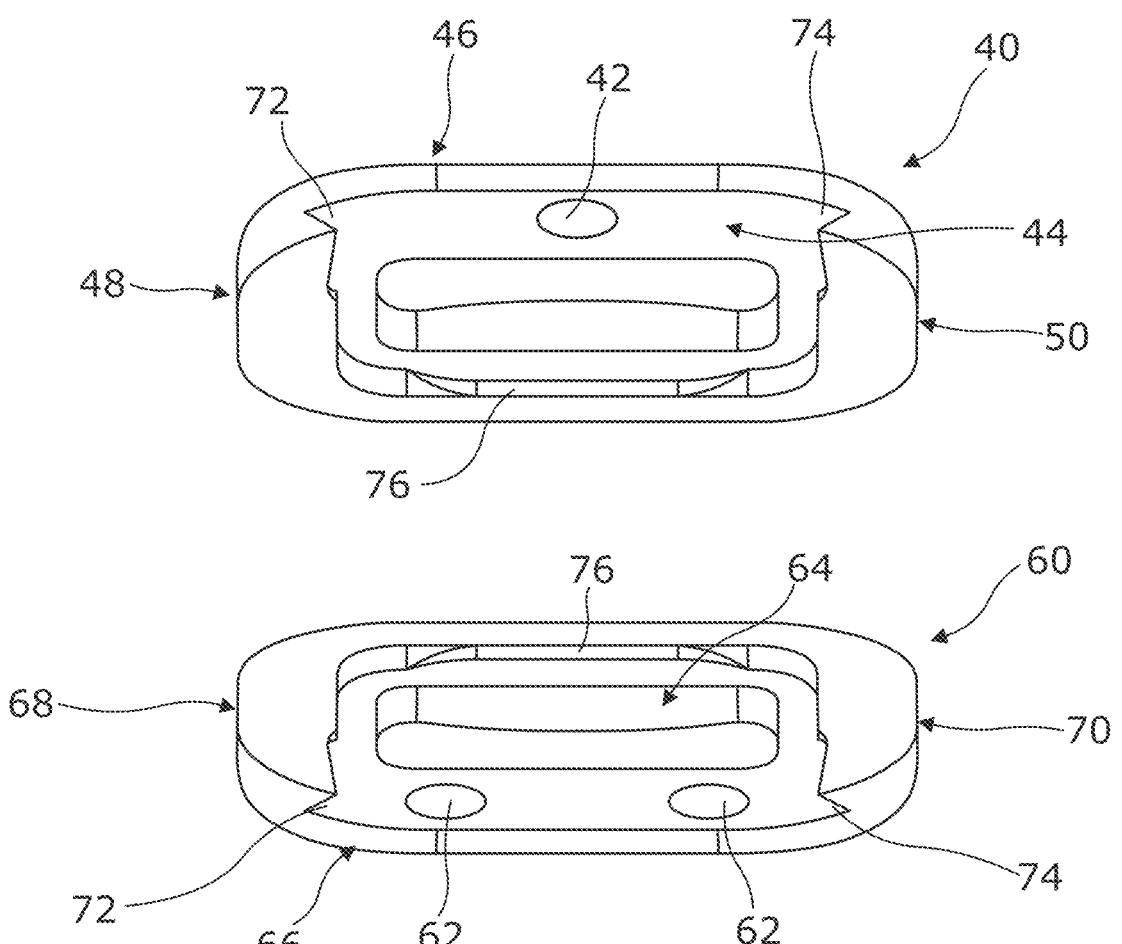
FIG. 2A shows the superior and inferior components of the first embodiment.
Figure 2B:
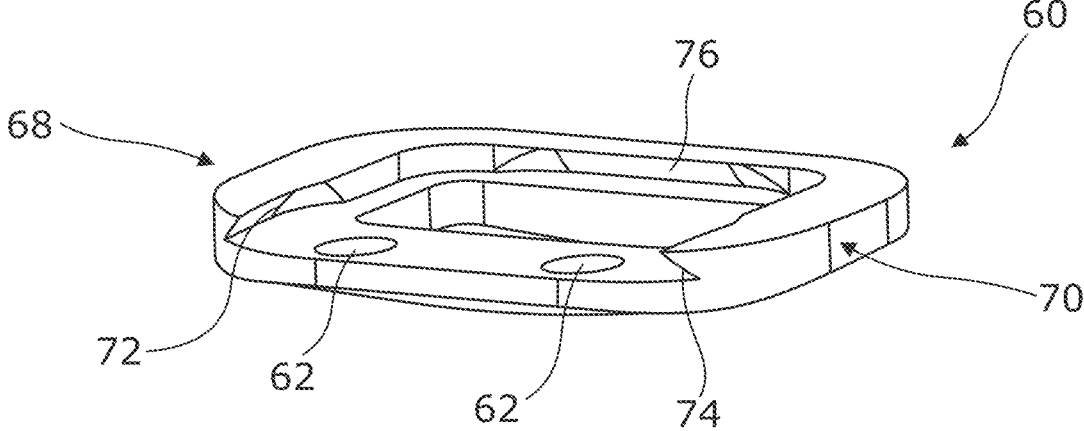
FIG. 2B is a perspective view from above, a lateral side and the anterior side of the inferior component of the first embodiment.

A core component 10, a superior component 40 and an inferior component 60 of a first embodiment of intervertebral fusion device are shown in FIGS. 1A to 2B. The intervertebral fusion device is an anterior lumbar interbody fusion (ALIF) device. A perspective view from above and the anterior side of the core component 10 is shown in FIG. 1A. A perspective view from above, a lateral side and the posterior side of the core component 10 is shown in FIG. 1B. A plan view and a view from the anterior side of the core component 10 are shown respectively in FIGS. 1C and 1D. FIG. 2A shows the superior 40 and inferior 60 components generally in the position in which the core component 10 is received between them. FIG. 2B is a perspective view from above, a lateral side and the anterior side of the inferior component 60. The superior and inferior components 40, 60 are the same as each other with the exception of the superior component having one aperture 42 therethrough and towards the anterior side whereas the inferior component has two apertures 62 therethrough, which are spaced apart from each other in the transverse direction and towards the anterior side. A perspective view of the inferior component 60 only of the superior and inferior components 40, 60 is therefore shown in the drawings.

As mentioned above, the intervertebral fusion device of the first embodiment comprises a superior component 40, an inferior component 60 and a core component 10. Each of the superior component 40 and the inferior component 60 is generally of the form of a plate, albeit a plate having structures thereon and a large aperture through the centre thereof. The core component 10 has the form of a frustum of a wedge. The intervertebral fusion device is assembled by putting the superior and inferior components 40, 60 in the disposition shown in FIG. 2A and then inserting the core component 10 between the superior and inferior components and such that the core component slidably inter-engages with the superior and inferior components, as is described further below. The superior and inferior components 40, 60 are held to the core component 10 by inter-engagement, as shown in FIG. 1E, with the core component determining the height of the intervertebral fusion device and the angle of the superior and inferior components relative to each other. Use of core components 10 of different thicknesses and/or different extents of tapering wedge and with the same superior component 40 and inferior component 60 provides for different heights and angles of intervertebral fusion device.

Considering assembly of the intervertebral fusion device further, the superior component 40 and the inferior component 60 are placed in the intervertebral space with the disposition shown generally in FIG. 2A. The core component 10 is positioned relative to the superior and inferior components 40, 60 such that the thinner edge of the wedge shape of the core is foremost before the core component is progressively inserted between the superior and inferior components until fully received between the superior and inferior components. When the intervertebral fusion device is assembled, the superior component top side abuts against a first vertebra defining the intervertebral space in part and the inferior component bottom side abuts against a second vertebra defining the intervertebral space in part.

According to an alternative approach to use of the intervertebral fusion device, the intervertebral fusion device is assembled outside the intervertebral space, as described above, before the assembled intervertebral fusion device is inserted into the intervertebral space.

The core component 10 will now be described further with reference to FIGS. 1A to 1D. As described above, the core component 10 has the form of a frustum of a wedge. The core component 10 has an upper side 12 and a lower side 14, the core component 10 being configured to be inserted between the superior and inferior components 40, 60 such that the upper side 12 faces the superior component bottom side and the lower side 14 faces the inferior component top side. The core component 10 has an anterior side, a posterior side, a first lateral side and a second lateral side. The anterior and posterior sides face in opposite directions and the first and second lateral sides face in opposite directions, with the first and second lateral sides being substantially orthogonal to the anterior and posterior sides. A transverse direction is between the first and second lateral sides. As mentioned above, the thinner posterior side is introduced first of the posterior and anterior sides between the superior and inferior components 40, 60.

The core component 10 comprises a rigid anterior component 16, which defines the anterior side and which has a box frame structure. The core component 10 also comprises a first lateral component 18, which defines the first lateral side, and a second lateral component 20, which defines the second lateral side. The first and second lateral components 18, 20 extend in substantially the same direction from a respective end of the rigid anterior component 16. The rigid anterior component 16, the first lateral component 18 and the second lateral component 20 are integrally formed. The core component 10 further comprises a posterior structure 22 which defines the posterior side. The posterior structure 22 comprises a first posterior component 24 and a second posterior component 26. The first posterior component 24 is integrally formed with and extends substantially orthogonally from the end of first lateral component 18 opposite the end from which the anterior component 16 extends. The second posterior component 26 is integrally formed with and extends substantially orthogonally from the end of the second lateral component 20 opposite the end from which the anterior component 16 extends. The distal ends of the first and second posterior components 24, 26 are spaced apart from and face each other. There is therefore a gap between the distal ends of the first and second posterior components 24, 26.

As may be seen from the plan view of FIG. 1C, the first and second lateral components 18, 20 taper slightly from the posterior side towards the anterior side. Each of the first and second lateral components 18, 20 is at an angle of taper of 2.5 degrees to an anterior to posterior axis of the core component. The anterior to posterior axis of the core component is indicated in FIG. 1C by the dashed line 28. When the core component 10 is as shown in FIGS. 1A to 1D it is in the expanded condition. The core component 10 is changed to the contracted condition by applying force to the first and second lateral components 18, 20 towards the posterior end to bend the first and second lateral components towards each other. Bending of the first and second lateral components 18, 20 towards each other moves the distal ends of the first and second posterior components towards each other to thereby reduce the gap between the distal ends and hence the width of the core component 10 towards the posterior end. Maximum bending of the first and second lateral components 18, 20 towards each other is achieved when the distal ends of the first and second posterior components abut each other.

An upper lateral protrusion 30 projects from each of the first and second lateral sides and a lower lateral protrusion 32 projects from each of the first and second lateral sides. The upper and lower lateral protrusions 30, 32 on the first lateral side are spaced apart from each other in a direction of separation of the upper and lower sides 12, 14 of the core component. The upper and lower lateral protrusions 30, 32 on the second lateral side are spaced apart from each other in a direction of separation of the upper and lower sides 12, 14 of the core component. Each lateral protrusion 30, 32 extends from the anterior side a part way towards the posterior side. As can be seen from FIG. 1B, the upper and lower lateral protrusions 30, 32 are at an angle corresponding to angulation of upper and lower sides 12, 14. Each lateral protrusion 30, 32 defines an inclined surface which extends from a distal edge of the lateral protrusion towards the core component.

The core component 10 comprises two upper 34 and two lower 36 posterior protrusions which project from the posterior side of the core component. The upper and lower posterior protrusions may be spaced apart from each other in a direction between the upper and lower sides of the core component. One of the upper posterior protrusions 34 and one of the lower posterior protrusions 36 projects from the first posterior component 24. The other of the upper posterior protrusions 34 and the other of the lower posterior protrusions 36 projects from the second posterior component 26. Each of the posterior protrusions 34, 36 extends about halfway along the posterior side from the distal end of its respective posterior component 24, 26. Each of the posterior protrusions 34, 36 defines an inclined surface which extends from a distal edge of the posterior protrusion towards the core component.

The superior and inferior components 40, 60 will now be described further with reference to FIGS. 2A and 2B. The superior component 40 has a superior component bottom side 44, a superior component top side 46, a first lateral side 48 and a second lateral side 50. The superior component 40 defines a circular aperture 42 towards its anterior edge. The circular aperture 42 allows for reception therethrough of a screw which is driven into the adjacent vertebra. The inferior component 60 has an inferior component top side 64, an inferior component bottom side 66, a first lateral side 68 and a second lateral side 70. The inferior component 60 defines two circular apertures 62 towards its anterior edge which are spaced apart from each other in the transverse direction. Each circular aperture 62 allows for reception therethrough of a screw which is driven into the adjacent vertebra. The superior component 40 defines formations on the superior component bottom side 44 and the inferior component 60 defines formations on the inferior component top side 64. The formations on the superior component bottom side 44 are the same as the formations on the inferior component top side 64. Therefore, the formations on the inferior component top side 64 will now be described on the understanding that their description applies also to the formations on the superior component bottom side 44.

The inferior component 60 defines first 72 and second keyways 74. The first keyway 72 is towards the first lateral side 68, the second keyway 74 is towards the second lateral side 70, and the first and second keyways oppose each other. Each of the first and second keyways 72, 74 is open at and extends from an anterior side of the inferior component 60 towards the posterior side of the component. Each keyway 72 is shaped to slidably receive a respective one of the lateral protrusions 30, 32 projecting from the core component 10. Thus, and now referring to the superior and inferior components 40, 60, the first keyway 72 on the superior compo-
nent 40 receives the upper lateral protrusion 30 on the first
lateral side of the core component 10, the second keyway 74
in the superior component 40 receives the upper lateral
protrusion 30 on the second lateral side of the core compo-
nent, the first keyway 72 on the inferior component receives
the lower lateral protrusion 32 on the first lateral side of the
core component 10, and the second keyway 74 on the
inferior component receives the lower lateral protrusion 32
on the second lateral side of the core component. Each
keyway 72, 74 extends from adjacent an anterior side of the
respective one of the superior and inferior components 40,
60 part way towards the posterior side and by a distance
corresponding to the distance extended by the respective
lateral protrusion 30, 32. Slidable reception of lateral pro-
trusions 30, 32 in keyways 72, 74 hold the superior com-
ponent 40, core component 10 and inferior component 60
together as the core component is slidably inserted between
the superior and inferior components.

Each keyway 72, 74 defines an inclined surface which
extends from a distal edge of the part of the superior or
inferior component defining the keyway in a transverse
direction away from the distal edge. The inclined surfaces of
the lateral protrusion 30, 32 and the keyway 72, 74 are of
corresponding angle whereby the two inclined surfaces abut
and allow for sliding movement of the core component 10
relative to the superior or inferior component 40, 60. The
first and second keyways 72, 74 on each of the superior and
inferior components 40, 60 taper in a direction from the
posterior side to the anterior side. The angle of taper is the
same as for the core component, i.e. 2.5 degrees to an
anterior to posterior axis of the superior/inferior component.
A distance between the first and second keyways 72, 74 is
therefore less at the anterior side than towards the posterior
side. As described above, the core component 10 tapers in
the same direction when in the expanded condition. The
inferior component 60 further defines a posterior recess 76
which extends between the first and second lateral sides 68,
70 near the posterior side. The posterior recess 76 has an
inclined surface.

When the core component is being inserted between the
superior and inferior components 40, 60, force is applied to
the first lateral component 18 and the second lateral com-
ponent 20 to bend the first and second lateral components
towards each other, as described above, to put the core
component in the contracted condition. Such compressive
force is applied by the leading ends of the first and second
lateral components 18, 20 bearing against the formations of
the superior and inferior components that define the first and
second keyways 72, 74 as the core component is inserted. In
the contracted condition, the core component can be slidably
received between the superior and inferior components 40,
60 with lateral protrusions 30, 32 received in keyways 72, 74
as described above. The spring bias of the first and second
lateral components 18, 20 releases the energy stored by the
applied force and causes the first and second lateral com-
ponents to spring apart and back to the expanded condition.
In the regained expanded condition the tapered lateral pro-
trusions 30, 32 on the core component 10 bear against the
tapered first and second keyways 72, 74 and such that they
oppose each other to a small extent in the posterior-anterior
direction to thereby present resistance to movement of the
core component relative to the respective one of the superior
and inferior components in a direction opposite to the
direction of insertion of the core component between the
superior and inferior components.

When the core component 10 is nearing full insertion
between the superior and inferior components 40, 60, the
distal edges of the posterior protrusions 34, 36 ride up the
inclined surfaces of their respective posterior recesses 76 to
draw the superior component 40 down onto the core com-
ponent and to draw the inferior component 60 up to the core
component. When the core component is fully inserted, a
wedge or screw (not shown) is driven between the gap
between the distal ends of the first and second posterior
components 24, 26 to keep the core component in the
expanded condition.

Figure 3A:
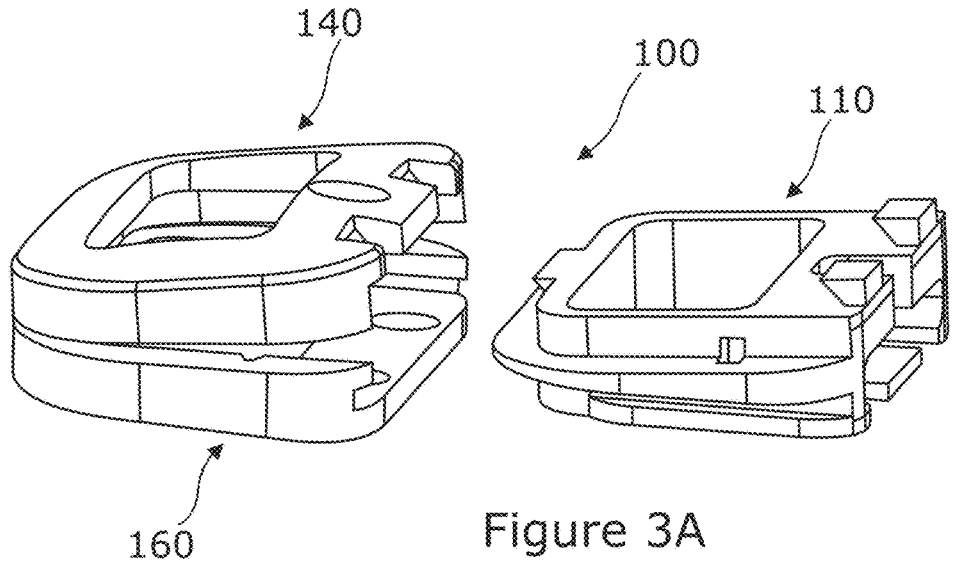
FIG. 3A is a perspective view from above and one side of a second embodiment of intervertebral fusion device.

A second embodiment of intervertebral fusion device 100
is shown in FIGS. 3A to 3G. Like the first embodiment, the
second embodiment of intervertebral fusion device 100
comprises a core component 110, a superior component 140
and an inferior component 160. FIG. 3A shows the core
component 110 when it is about to be inserted between the
superior and inferior components 140, 160. Use of the
second embodiment of intervertebral fusion device 100 is
the same as the first embodiment of intervertebral fusion
device described above. The second embodiment of
intervertebral fusion device 100 differs from the first
embodiment of intervertebral fusion device primarily in
respect of how the core component 110 is retained between
the superior and inferior components 140, 160 after inser-
tion. The second embodiment of intervertebral fusion device
100 also differs from the first embodiment of intervertebral
fusion device in respect of how the core component 110
inter-engages with the superior and inferior components
140, 160. As will become apparent from the following
description, the formations of the second embodiment which
provide for inter-engagement differ from the formations of
the first embodiment which provide for inter-engagement.

Figure 3B:
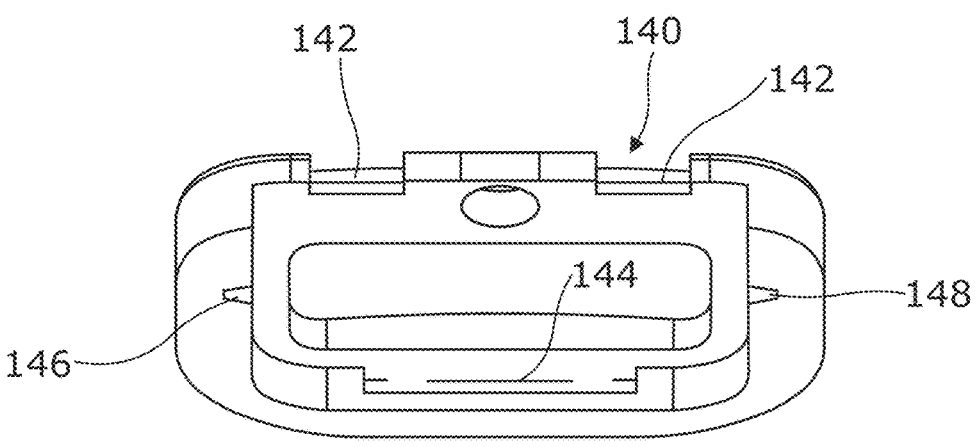
FIG. 3B is a view of the superior component of the second embodiment.
Figure 3C:
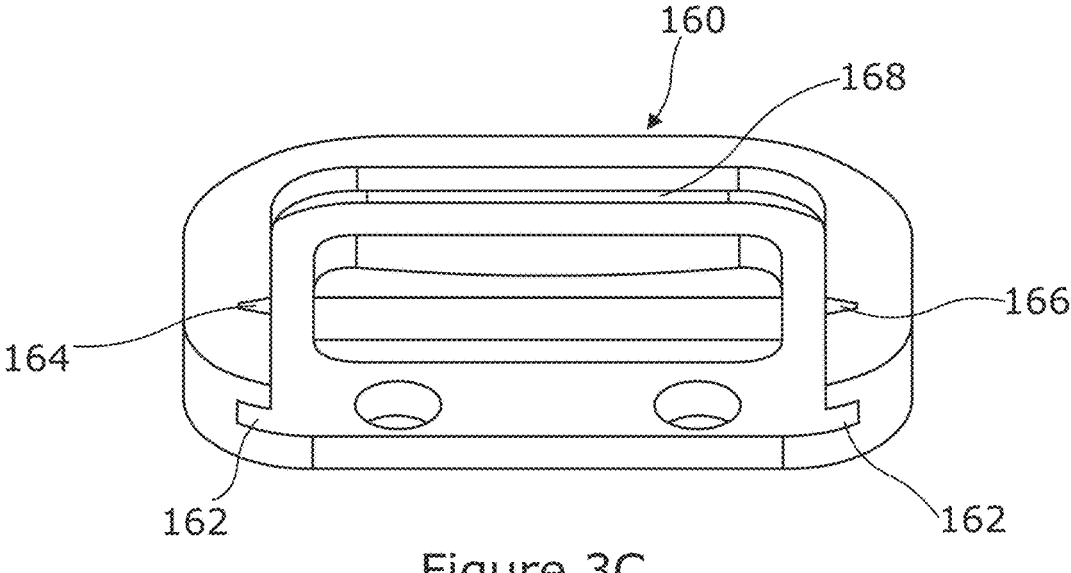
FIG. 3C is a view of the inferior component of the second embodiment.

The superior component 140 of the second embodiment is
shown in FIG. 3B and the inferior component 160 of the
second embodiment is shown in FIG. 3C. The superior and
inferior components 140, 160 of the second embodiment are
of the same form as the superior and inferior components 40,
60 of the first embodiment except as will now be described.

The superior component 140 defines two anterior inter-
engaging recesses 142 spaced apart along the anterior side.
The superior component 140 also defines a posterior inter-
engaging recess 144 towards the posterior side. Further to
this, the superior component 140 defines first 146 and
second 148 retention mechanism recesses. The first retention
mechanism recess 146 is towards a first lateral side of the
superior component 140 and the second retention mecha-
nism recess 148 is towards a second lateral side of the
superior component with the first and second retention
mechanism recesses facing each other in the transverse
direction. In this embodiment, the core component 110 has
parallel sides and the superior and inferior components 140,
160 are correspondingly configured.

The inferior component 160 defines two lateral channels
162. One of the two lateral channels 162 is towards the first
lateral side and the other of the two lateral channels 162 is
towards the second lateral side, with the two lateral channels
facing each other in the transverse direction. Each of the two
lateral channels 162 is open at the anterior side and extends
towards the posterior side. The inferior component 160 also
defines third 164 and fourth 166 retention mechanism
recesses. The third retention mechanism recess 164 is
towards a first lateral side of the inferior component 160 and
the fourth retention mechanism recess 166 is towards a
second lateral side of the inferior component with the third
and fourth retention mechanism recesses facing each other
in the transverse direction. Each of the third and fourth retention mechanism recesses 164, 166 is defined by the part of the inferior component 160 that defines the upper side of the lateral channel whereby the retention mechanism recesses 164, 166 is above the lateral channel.

Turning now to the core component 110 shown in FIGS. 3D and 3F, the core component of the second embodiment is of the same form as the core component 10 of the first embodiment except as will now be described. The core component 110 of the second embodiment comprises two anterior inter-engaging protrusions 112 spaced apart along the anterior side. The core component 110 also defines first and second posterior inter-engaging protrusions 114, 115 towards the posterior side. When the core component 110 is inserted between the superior and inferior components 140, 160, the first posterior inter-engaging protrusion 114 inter-engages with the posterior inter-engaging recess 144 on the superior component, the second posterior inter-engaging protrusion 115 inter-engages with a posterior inter-engaging recess 168 on the inferior component, and the two anterior inter-engaging protrusions 112 inter-engage respectively with the two anterior inter-engaging recesses 142 on the superior component to pull the superior component down onto the core component. The core component 110 further defines two elongate protrusions 116. One of the two elongate protrusions 116 is at the first lateral side and the other of the two elongate protrusions 116 is at the second lateral side, with the two elongate protrusions protruding in opposite directions and in the transverse direction. Each of the two elongate protrusions 116 extends from the anterior side to the posterior side. As is shown in FIG. 3G, each of the two elongate protrusions 116 of the core component 110 is slidably received in a respective one of the two lateral channels 162 of the inferior component 160 whereby the core component and the inferior component slidably inter-engage.

The retention mechanism of the second embodiment will now be described. The retention mechanism comprises a straight sprung member 170 formed of the like of MP35N. The sprung member 170 is mounted on the core component such that it extends in the transverse direction. When the sprung member 170 is unbent and as shown in FIGS. 3D and 3E, a first end of the sprung member extends through a slot in the core component such that it protrudes beyond the periphery of the core component at the first lateral side and a second, opposite end of the sprung member extends through a slot in the core component such that it protrudes beyond the periphery of the core component at the second lateral side. The height of the sprung member 170 between the upper and lower sides of the core component and the supporting of the sprung member by the core component are such that the first and second ends of the sprung member face both the superior and inferior components.

Figures 3D, 3E, 3F, 3G:
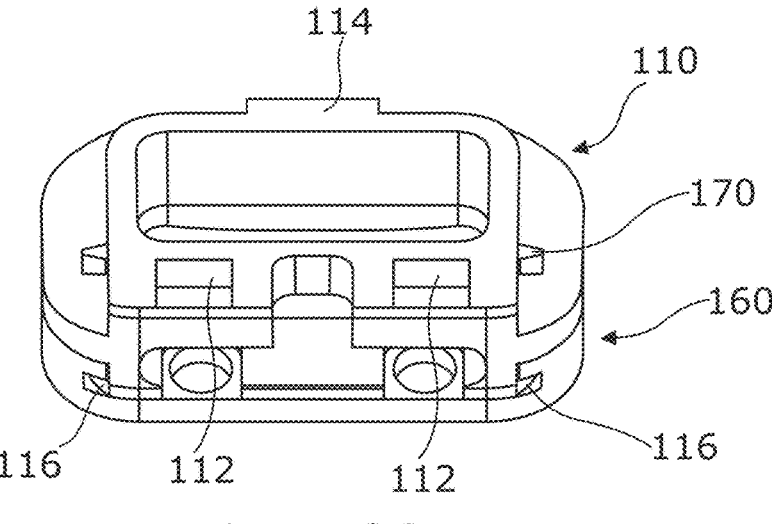
FIG. 3D is a view of the core component of the second embodiment when viewed from the posterior side.
FIG. 3E is a view of the sprung member of the second embodiment.
FIG. 3F is a view of the core component of the second embodiment when viewed from above.
FIG. 3G shows the core component when inter-engaged with the inferior component according to the second embodiment.

When the sprung member 170 is bent upon application of a bending force and as shown in FIG. 3F, the first and second ends of the sprung member are withdrawn through their respective slots whereby neither of the first and second ends protrudes beyond the periphery of the core component at its respective lateral side. The retention mechanism is in its expanded condition when the sprung member 170 is unbent as shown in FIG. 3D and the retention mechanism is in its contracted condition when the sprung member 170 is bent as shown in FIG. 3F.

When the core component 110 is being inserted between and being brought into inter-engagement with the superior and inferior components 140, 160, as described above, a bending force is applied to the sprung member 170 to put it in the contracted condition as shown in FIG. 3F. This allows the two elongate protrusions 116 of the core component to slide along the two lateral channels 162 of the inferior component 160 until the first and second ends of the sprung member 170 are in registration with the first to fourth retention mechanism recesses 146, 148, 164, 166 in the superior and inferior components 140, 160. The sprung member 170 returns to its unbent state whereby the first and second ends are pushed into their respective retention mechanism recesses 146, 148, 164, 166. Reception of the first and second ends in retention mechanism recesses 146, 148, 164, 166 presents resistance to movement of the core component 110 from between the superior and inferior components 140, 160.

Figures 4, 5A, 5B:
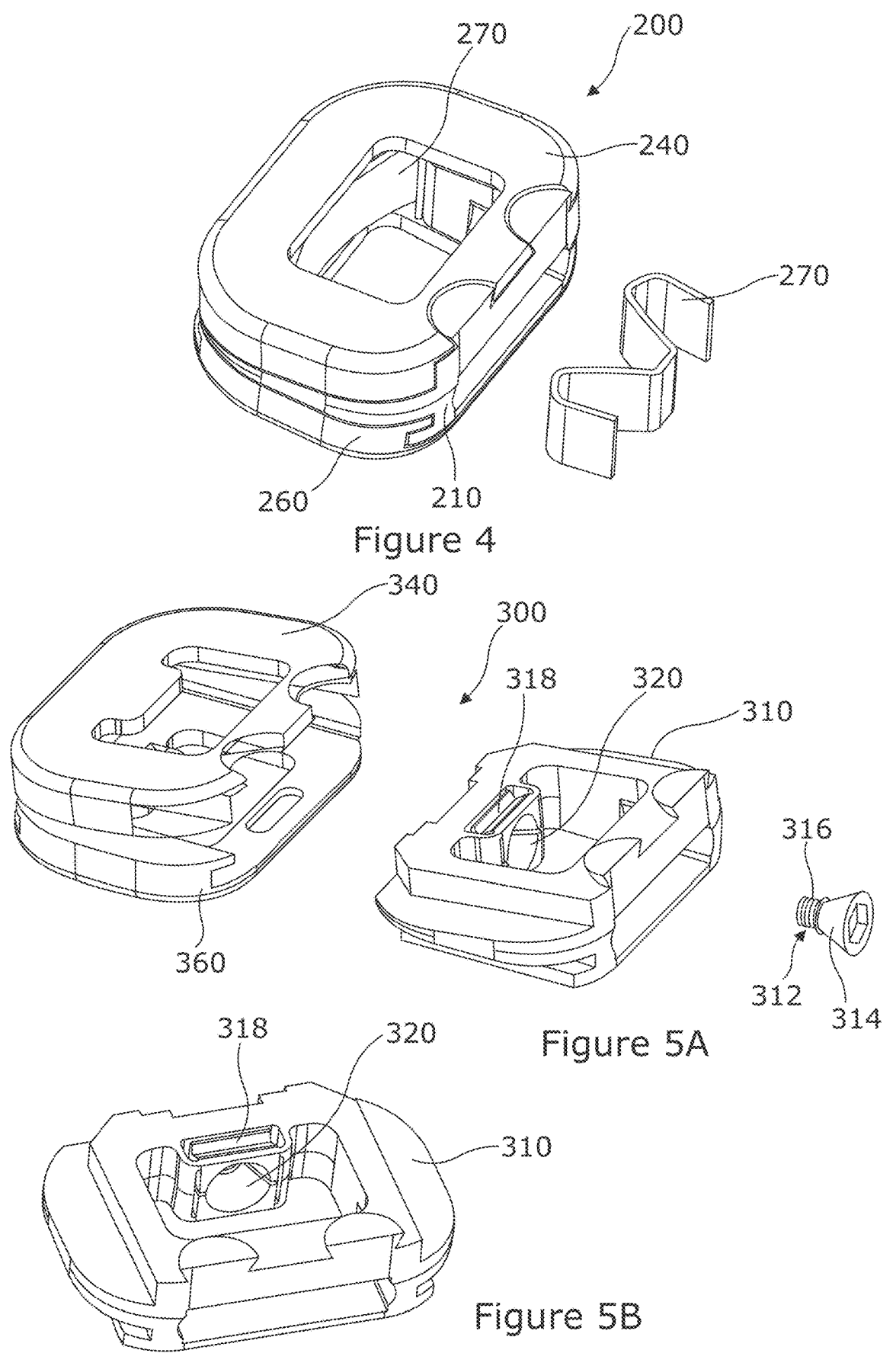

A third embodiment of intervertebral fusion device 200 is shown in FIG. 4. The third embodiment of intervertebral fusion device 200 is of the same form and function as the second embodiment of intervertebral fusion device 100 except as is described below. The third embodiment of intervertebral fusion device 200 comprises a core component 210, a superior component 240 and an inferior component 260. Inter-engagement of the core component 210 with the superior and inferior components 240, 260 is by way of structure common with the second embodiment. Also, the third embodiment of intervertebral fusion device 200 is brought into use in the same fashion as the first and second embodiments. The reader's attention is therefore directed to the description provided above for the second embodiment in respect of such common form and function and to the description provided above for the first embodiment in respect of use.

Turning now to differences between the second and third embodiments, the third embodiment has a shaped sprung member 270 formed of MP35N instead of the straight sprung member 170 of the second embodiment. FIG. 4 shows the shaped sprung member 270 to the right-hand side of the assembled intervertebral fusion device 200 and in its form when removed from the core component 210. The shaped sprung member 270 is mounted in the core component such that it is in the same shaped condition as shown in FIG. 4. This constitutes the contracted condition in which the core component 210 can be inserted between and brought into inter-engagement with the superior and inferior components 240, 260. When the core component has been fully received between the superior and inferior components 240, 260, a bending force is applied to the shaped sprung member 270 which causes the shaped sprung member to lengthen. Lengthening of the shaped sprung member 270 causes first and second opposite ends of the shaped sprung member to slide through slots in the core component 210 whereby the first and second ends of the shaped sprung member protrude beyond the periphery of the core component at the first and second lateral sides. When the first and second ends of the shaped sprung member 170 protrude in this fashion and as shown in the assembled intervertebral fusion device 200 shown in FIG. 4, they are received in respective retention mechanism recesses in the superior and inferior components 240, 260. Reception of the first and second ends of the shaped sprung member 170 in retention mechanism recesses presents resistance to movement of the core component 210 from between the superior and inferior components 240, 260 in the same manner as for the second embodiment.

As can been seen from the assembled intervertebral fusion device 200 shown in FIG. 4, the shaped sprung member 270 is in a bowed condition. The shaped sprung member 270 is structured and supported in the core component 210 such that the shaped sprung member 270 is distorted by the applied bending force to the extent that it has the shown bowed condition. When in the bowed condition, a bending force needs to be applied in the opposite direction to the above described first applied bending force to return the shaped sprung member 270 to its original and contracted condition. The need for application of force to change the shaped sprung member 270 from its bowed to its original condition keeps the retention mechanism formed by way of the shaped sprung member 270 in the expanded condition.

A fourth embodiment of intervertebral fusion device 300 is shown in FIGS. 5A and 5B. The fourth embodiment of intervertebral fusion device 300 is of the same form and function as the second embodiment of intervertebral fusion device 100 except as is described below. The fourth embodiment of intervertebral fusion device 300 comprises a core component 310, a superior component 340 and an inferior component 360. Inter-engagement of the core component 310 with the superior and inferior components 340, 360 is by way of structure common with the second embodiment. Also, the fourth embodiment of intervertebral fusion device 300 is brought into use in the same fashion as the first and second embodiments. The reader's attention is therefore directed to the description provided above for the second embodiment in respect of such common form and function and to the description provided above for the first embodiment in respect of use.

Turning now to differences between the second and fourth embodiments, the retention mechanism of the fourth embodiment 300 comprises a screw 312 (which constitutes a driving device). The screw 312 defines a first frustroconical surface 314 and a first threaded portion 316. The retention mechanism of the fourth embodiment 300 also comprises first 318 and second 320 retention mechanism portions. Each of the first and second retention mechanism portions 318, 320 is mounted towards the posterior end of the core component 310 for rotation on the core component. The first retention mechanism portion 318 defines a first part of a second frustroconical surface and the second retention mechanism portion 320 defines a second part of the second frustroconical surface. The first and second retention mechanism portions 318, 320 are located such that the first and second parts of the second frustroconical surface oppose each other. The first and second parts of the second frustroconical surface together define the second frustroconical surface, albeit with a gap between the first and second retention mechanism portions.

Before the screw 312 is brought into use, the first and second retention mechanism portions 318, 320 do not protrude beyond the periphery of the upper and lower sides of the core component. This constitutes the contracted condition of the retention mechanism of the fourth embodiment and in which the core component 310 can be inserted between and brought into inter-engagement with the superior and inferior components 340, 360.

When the core component 310 is fully received between the superior and inferior components 340, 360, the screw 312 is brought into use. The screw 312 is inserted through an aperture at the anterior side of the core component and then positioned such that the first threaded portion 316 is received between the first and second retention mechanism portions 318, 320 in the space defined by the second frustroconical surface. Upon further insertion, the screw 312 is received through an aperture defined by the first and second retention mechanism portions 318, 320 at the base of the second frustroconical surface and then threadedly engages with a second threaded portion (not evident from FIGS. 5A and 5B) defined by part of the core component which is located closer to the posterior side of the core component than the first and second retention mechanism portions. Rotation of the screw 312 therefore causes the screw 312 to move linearly in relation to the first and second retention mechanism portions 318, 320 and towards the posterior end. Movement of the screw 312 towards the posterior end causes the first frustroconical surface 314 of the screw to push against the second frustroconical surface defined by the first and second retention mechanism portions 318, 320. Pushing of the first frustroconical surface 314 of the screw against the second frustroconical surface pushes the first and second retention mechanism portions 318, 320 apart. In view of the first and second retention mechanism portions 318, 320 being rotatably mounted on the core component, pushing apart of the first and second retention mechanism portions causes a distal portion of the first retention mechanism portion 318 to protrude beyond the periphery of the upper side of the core component 310 and to be received in a first retention mechanism recess defined in the superior component bottom side of the superior component 340. Also, pushing apart of the first and second retention mechanism portions causes a distal portion of the second retention mechanism portion 320 to protrude beyond the periphery of the lower side of the core component 310 and to be received in a second retention mechanism recess defined in the inferior component top side of the inferior component 360. This constitutes the expanded condition of the retention mechanism of the fourth embodiment in which resistance to movement of the core component 310 from between the superior and inferior components 340, 360 is presented.

The invention claimed is:

1. An intervertebral fusion device comprising:

a superior endplate;

an inferior endplate, the superior and inferior endplates configured to be received in an intervertebral space between first and second vertebrae;

a core component configured for insertion between the superior and inferior endplates whereby a separation between the superior and inferior endplates is determined; and a retention mechanism comprised in the core component, wherein:

the retention mechanism comprises first and second retention mechanism portions which are movable relative to each other between a contracted condition and an expanded condition, the first and second retention mechanism portions are closer together in the contracted condition whereby the first and second retention mechanism portions do not protrude beyond a periphery of the core component at its upper and lower sides respectively, the core component insertable between the superior and inferior endplates when in the contracted condition, and the first and second retention mechanism portions are further apart in the expanded condition whereby the first and second retention mechanism portions protrude beyond the periphery of the core component at its upper and lower sides respectively, the first and second retention mechanism portions interengaging respectively with the superior and inferior endplates when in the expanded condition and when the core component is received between the superior and inferior endplates to thereby present resistance to movement of the core component from between the superior and inferior endplates.

2. The intervertebral fusion device according to claim 1, wherein the first retention mechanism portion is received in a first retention mechanism recess in the superior endplate and the second retention mechanism portion is received in a second retention mechanism recess in the inferior endplate when the first and second retention mechanism portions are in the expanded condition.

3. The intervertebral fusion device according to claim 1, wherein the retention mechanism has a spring bias which biases the first and second retention mechanism portions apart towards the expanded condition.

4. The intervertebral fusion device according to claim 3, wherein the retention mechanism comprises a sprung member which provides the spring bias.

5. The intervertebral fusion device according to claim 1, wherein the retention mechanism comprises a driving device which cooperates with the first and second retention mechanism portions to push the first and second retention mechanism portions apart to thereby move the retention mechanism to the expanded condition.

6. The intervertebral fusion device according to claim 1, wherein the retention mechanism is located towards a posterior end of the core component whereby the first and second retention mechanism portions are towards the posterior end of the core component and protrude respectively from the upper and lower sides of the core component when in the expanded condition.

7. The intervertebral fusion device according to claim 1, wherein the first and second retention mechanism portions are located in the core component substantially midway in a medial-lateral direction of the core component.

8. The intervertebral fusion device according to claim 7, wherein the first and second retention mechanism portions oppose each other.

9. The intervertebral fusion device according to claim 8, wherein the first and second retention mechanism portions remain substantially in registration with each other when the core component is viewed from above or below and when the first and second retention mechanism portions move between the contracted and expanded conditions.

10. The intervertebral fusion device according to claim 1, wherein the first and second retention mechanism portions move bodily together and apart between the contracted and expanded conditions.

11. The intervertebral fusion device according to claim 1, wherein the core component is integrally formed and the retention mechanism is integral to the core component.

12. The intervertebral fusion device according to claim 1, wherein surface profiles of the core component slidably inter-engage with surface profiles of the inferior endplate to present a barrier to movement of the inferior endplate away from the core component in a direction of separation of the superior and inferior endplates from each other and as the core component is slidably received between the superior and inferior endplates.

13. The intervertebral fusion device according to claim 12, wherein the core component comprises a first lateral protrusion projecting from a first lateral side of the core component and a second lateral protrusion projecting from a second lateral side of the core component, the inferior endplate defines first and second keyways respectively towards first and second lateral sides of the inferior endplate, the first and second keyways opposing each other, and each of the first and second keyways is shaped to slidably receive a respective one of the first and second lateral protrusions.

14. The intervertebral fusion device according to claim 13, wherein each of the first and second keyways extends from an anterior end of the inferior endplate towards a posterior end of the inferior endplate.

15. The intervertebral fusion device according to claim 1, wherein the superior endplate, the inferior endplate and the core component are separate components, the superior and inferior endplates not engaging with each other other than by way of the core component.

16. A method of installing an intervertebral fusion device in an intervertebral space between first and second vertebrae, the intervertebral fusion device comprising a superior endplate, an inferior endplate, a core component and a retention mechanism comprised in the core component, the retention mechanism comprising first and second retention mechanism portions which are movable relative to each other between a contracted condition and an expanded condition, the method comprising:

positioning the superior and inferior endplates relative to each other such that a bottom side of the superior endplate and a top side of the inferior endplate oppose each other;

inserting the core component between the superior and inferior endplates whereby a separation between the superior and inferior endplates is determined; and disposing the intervertebral fusion device in the intervertebral space, wherein:

the first and second retention mechanism portions are closer together in the contracted condition whereby the first and second retention mechanism portions do not protrude beyond a periphery of the core component at its upper and lower sides respectively, the core component insertable between the superior and inferior endplates when in the contracted condition, and the first and second retention mechanism portions are further apart in the expanded condition whereby the first and second retention mechanism portions protrude beyond the periphery of the core component at its upper and lower sides respectively, the first and second retention mechanism portions interengaging respectively with the superior and inferior endplates when in the expanded condition and when the core component is received between the superior and inferior endplates to thereby present resistance to movement of the core component from between the superior and inferior endplates.

17. The method according to claim 16, wherein the intervertebral fusion device is installed in the intervertebral space by positioning the superior and the inferior endplates relative to each other in the intervertebral space and before the core component is inserted between the superior and inferior endplates.

18. The method according to claim 16, wherein the intervertebral fusion device is installed in the intervertebral space by positioning the superior and inferior endplates relative to each other at a location apart from the intervertebral space and inserting the core component between the superior and inferior endplates at the location apart from the intervertebral space and before the thus assembled intervertebral fusion device is installed in the intervertebral space.

* * * * *